United States Patent [19]

Isaacson et al.

[11] Patent Number: 5,588,429
[45] Date of Patent: Dec. 31, 1996

[54] PROCESS FOR PRODUCING OPTIMAL CURRENT PATTERNS FOR ELECTRICAL IMPEDANCE TOMOGRAPHY

[75] Inventors: David Isaacson, Latham; Margaret Cheney, Troy, both of N.Y.

[73] Assignee: Rensselaer Polytechnic Institute, Troy, N.Y.

[21] Appl. No.: 317,678

[22] Filed: Oct. 5, 1994

Related U.S. Application Data

[63] Continuation-in-part of Ser. No. 734,591, Jul. 23, 1991, Pat. No. 5,381,333, Ser. No. 727,075, Jul. 9, 1991, Pat. No. 5,390,110, and Ser. No. 132,457, Oct. 6, 1993, Pat. No. 5,544,662.

[51] Int. Cl.$^6$ ............................................. A61B 5/05
[52] U.S. Cl. .............................................. 128/734
[58] Field of Search .............................. 128/734, 741, 128/693; 364/413.02, 413.13, 413.15

[56] References Cited

U.S. PATENT DOCUMENTS

| | | | |
|---|---|---|---|
| 4,617,939 | 10/1986 | Brown et al. | 128/734 |
| 4,649,932 | 3/1987 | Smith | 128/734 |
| 4,920,490 | 4/1990 | Isaacson | 128/734 X |
| 5,272,624 | 12/1993 | Gisser et al. | 128/734 X |

Primary Examiner—Angela D. Sykes
Attorney, Agent, or Firm—Notaro & Michalos P.C.

[57] ABSTRACT

In electrical impedance tomography systems, the precision of voltage measurement is a critical factor in the results. Usually, the voltage values to be measured are limited by the necessity of limiting currents through the body to safe values. An effective method for increasing the apparent precision of the voltmeters is to use non-sinusoidal current patterns that produce the largest voltage variations in regions of most importance. This invention discloses several improvements in the methods by which the images resulting from any system of hardware that permits simultaneous injection of currents to all electrodes and voltage measurements at all electrodes, may be improved. One such improvement is a technique to find the shapes of the best current patterns to distinguish two different distributions of admittivity, conductivity, and permittivity in the region surrounded by electrodes. Another is a more complex procedure for finding the best shapes of the current patterns to best characterize an unknown pattern of admittivity, conductivity, or permittivity. Yet another is a procedure for calculating the values of voltages that would have been measured had sinusoidal sets of current been used, when actually using non-sinusoidal current patterns. This permits any standard reconstruction algorithm based on sinusoidal currents to be used with non-sinusoidal currents.

2 Claims, 5 Drawing Sheets

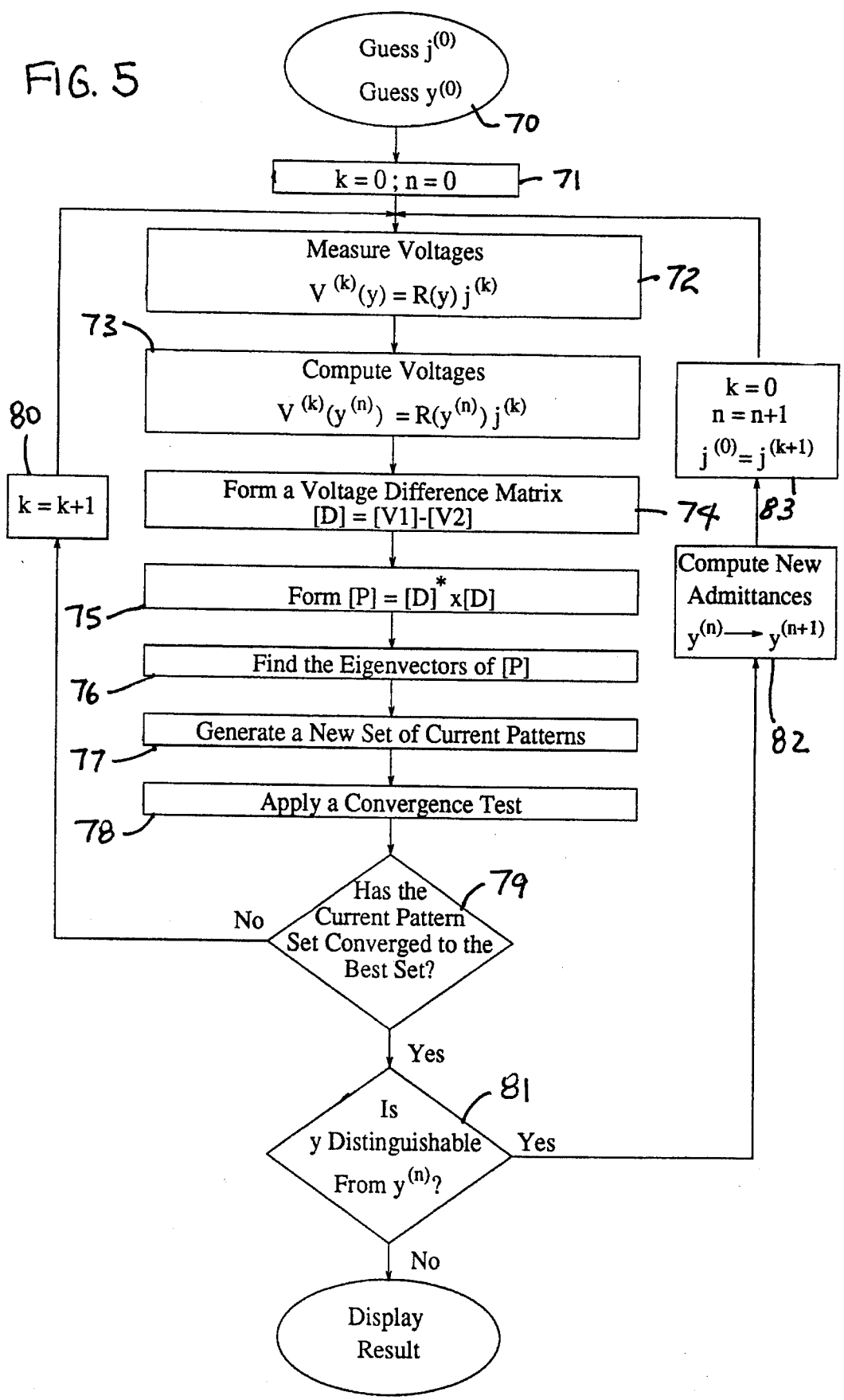

PROCESS FOR PRODUCING OPTIMAL CURRENT PATTERNS FOR ELECTRICAL IMPEDANCE TOMOGRAPHY

CROSS REFERENCE TO RELATED APPLICATIONS

The present application is a continuation-in-part of U.S. patent application Ser. Nos. 07/734,591 filed Jul. 23, 1991, now U.S. Pat. No. 5,381,333, 07/727,075 filed Jul. 9, 1991, now U.S. Pat. No. 5,390,110, and 08/132,457 filed Oct. 6, 1993, now U.S. Pat. No. 5,544,662.

FIELD AND BACKGROUND OF THE INVENTION

The present invention relates in general to the field of electrical impedance tomography and in particular to new and useful methods for the selection of the current pattern or patterns best suited for use in implementing certain impedance tomography systems when specific goals for the system are known. While the apparatus and methods shown here are intended for use in the medical area for distinguishing internal structures of the human body non-invasively, many other applications exist for systems with these capabilities in areas such as flaw detection, geology, food and other material processing, etc.

An apparatus for practicing electric impedance tomography is disclosed in an article by the coinventors of the present invention, entitled "An Electric Current Tomograph", IEEE TRANSACTIONS ON BIOMEDICAL ENGINEERING, Vol. 35 No. 10, October, 1988. A process and apparatus for utilizing a similar array of electrodes in electrical impedance tomography is disclosed in U.S. Pat. No. 4,920,490, granted to one of the Coinventors of the present invention. U.S. Pat. No. 4,920,490 is incorporated here by reference, and discloses a means to determine the shape of a single current pattern that best distinguishes the presence of a region of any conductivity inside a body different from a known uniform conductivity or of any two conductivity distributions from each other.

The parent U.S. patent application Ser. No. 07/734,591 to the present case, teaches a method for utilizing the same apparatus to determine the values, point by point, of an unknown distribution of conductivities present inside a body by finding the complete set of optimal current patterns required to best distinguish the unknown distribution from an arbitrary guessed distribution and then from successively closer approximations to the actual distribution. This iterative process requires a method for calculating the voltage to be expected at each electrode for each conductivity distribution and each set of current patterns used. This process may be used to find a conductivity distribution that may then be presented to a user in the form of a cross-sectional image, or conductivity map.

All impedance measurements have two attributes, a real, or in-phase component related to energy loss, which results in resistive information and the imaginary, or quadrature component which result in reactive information related to energy storage. The magnitude of the specific impedance of an element of a body is given by the square root of the sum of the squares of the resistivity and reactivity of that element where the resistivity and reactivity are considered series elements.

In a similar way the reciprocal of the specific impedance magnitude, the admittivity magnitude, is the square root of the sum of the squares of the conductivity and susceptivity, which are considered as elements in parallel. The susceptivity, is the angular frequency times the permittivity. Since the permittivity is more constant with frequency than other reactive terms in most materials, and is so easily related to them, it is the quantity of choice, along with conductivity and admittivity, the phasor sum of the conductivity and susceptivity. Conductivity and susceptivity may easily be calculated from resistivity and reactivity values.

When using an impedance imaging system, an apparatus for finding information about the interior of a body using measurements made on its surface, one might have any of several goals. If one were only concerned with whether the area being examined was uniform and homogeneous or whether it contained some inhomogeneity, such as an internal crack in a metal sample, and if detecting the presence of the crack were the only goal, then one need apply only a single spatial pattern of currents to the electrodes. The question of what should be its shape was answered by Isaacson in U.S. Pat. No. 4,920,490.

In many applications of impedance imaging it is not sufficient to determine that some region has an impedance distribution different from that expected. Instead, one would like to produce a fully reconstructed image of the admittance pattern in the region of interest. The number of picture elements desired usually exceeds the number of electrodes used, so it is necessary to apply not one, but many independent spatial current patterns to the electrodes. The number of independent patterns is limited to less than the number of electrodes, so that, for instance, in a 32 electrodes system 31 patterns may be sequentially applied, resulting in 31×32 or 992 separate voltage measurements for real, an equal number for reactive, and a maximum of 496 picture elements.

The user of the system nearly always wishes for the best possible images. These require many electrodes and the best possible current stability and measurement precision. When used with humans, there are limits to the maximum currents or powers that may be employed. Improvement in effective signal-to-noise ratio of the voltmeters can be produced by the use of current patterns whose shapes force more current to flow through regions of the sample of special interest. Unfortunately, adaptive methods that produce optimal current patterns for improved images require considerable time for both calculations and many repetitive data measurements. Whenever the fastest possible acquisition and processing of image data is needed for cylindrical geometry, it is most expedient to use the full set of sinusoidal current patterns, of increasing spatial frequency, which we designate the canonical patterns. Along with these, an approximate solution for the distribution of admittivities in the sample based on the canonical current patterns applied and the voltages measured has been developed. It is based on the first step of Newtons method, and designated is NOSER.

SUMMARY OF THE INVENTION

The present invention discloses a novel procedure for finding the full set of orthogonal current patterns for best distinguishing two separate admittivity distributions from each other. This can be followed by a reduction of the optimal current patterns into their sinusoidal components, which may then be converted to patterns of admittivity using NOSER if the measured voltages are appropriately scaled. This could be called a non-adaptive reconstruction method using adaptive current patterns. Although the time required for the initial adaptive steps may be high, the time required for reconstruction of a set of consecutive similar images made with the same patterns could be quite small. The overall advantage is the effective improvement in the ratio of signal to noise of the measured voltages.

There are times when the very best possible images are required regardless of time or calculation difficulty. The approach disclosed in parent patent application Ser. No. 07/734,591 for conductivity image patterns is here extended to admittivity images. First a complete set of optimal current patterns are produced adaptively from an initially guessed set, usually the canonical ones, and an initial guess for the admittivity distribution, usually uniform. Then a distribution of admittivities is calculated for that optimal set. This distribution is almost certainly closer to the real distribution than the initial guess, but can be further improved. The system now adaptively finds the optimal set of current patterns to distinguish the measured admittivity distribution from the last calculated one. This process is repeated until differences are below a preset threshold. Images of admittivity magnitude or angle, permittivity, or conductivity can then be displayed.

Some systems for impedance tomography apply currents to one adjacent pair of electrodes at a time and measure the voltages at all other electrodes during each application of current. Others, including the present invention, measure all voltages while the current is applied simultaneously to all of the electrodes. Since the sum of the currents is constrained to zero, some electrode-currents must have negative polarity. The currents applied are all of the same frequency and phase, except for the required polarity reversal, but their magnitudes are different for different electrodes, resulting in a current pattern, or plot of current magnitude versus electrode number, that can have almost any shape, but whose maximum slope is to the change in current from maximum positive to maximum negative at adjacent electrodes.

In order to obtain the maximum information about the distribution of electrical quantities within the region surrounded by the electrodes, more than one current pattern must be applied. For the information to be non-redundant, all of the current patterns applied should be orthogonal to each other. If the simplest set of current patterns, the sines and cosines of lowest spatial frequency are used, additional orthogonal patterns are sines and cosines of n times the lowest spatial frequency, where n=1, 2, 3, ... The maximum value of n is limited, however to the frequency where adjacent electrodes have alternating maximum positive and maximum negative currents, which is an approximation to a cosine. The spatial sine of the same frequency, however, applies zero currents to all electrodes and is therefore not useful.

Useful systems have been employed using sine and cosine current patterns of all frequencies possible, and reconstruction algorithms that are quite fast have been implemented to display images of distributions of several electrical quantities. However, in order to produce "snapshot" images of moving objects, such as the heart and lungs, it is necessary to complete the application of all of the current patterns and the measurement of all of the voltages for each pattern in a time short enough so that the object is quasi-stationary. The signal-to-noise ratio of the voltmeters is proportional to their signal acquisition time, so it becomes limited in such high-speed systems. The simplest way to increase the signal, by increasing the current magnitudes, is forbidden in human subjects.

Another way to improve the apparent signal-to-noise ratio is to use current patterns that are not sinusoidal (but have the same maximum current values). For every distribution of admittivities in a region of investigation, there is a particular set of orthogonal current patterns that are non-sinusoidal and of such shapes to cause higher currents to flow in areas of the region containing inhomogeneities than in relatively homogeneous regions, thus resulting in larger voltages to be measured at some of the electrodes. A method for finding such "best" current patterns for distinguishing between two different distributions of admittivity (such as those for the thorax with lungs nearly full and partially empty) is described in detail below and forms one part of the present invention.

An additional part of the invention is an improved method for finding the optimal non-sinusoidal set of current patterns to apply to an unknown sample, along with the unknown admittivity distribution. This procedure requires both a "forward" solver, that is, a method for calculating the voltages that should appear at the electrodes theoretically when a known current pattern is applied to a known admittivity distribution, and an "inverse" solution algorithm. The inverse problem is finding the admittivity distribution inside when the electrode currents and voltages are known.

The procedure involves first guessing an admittivity distribution, such as a homogeneous one, and applying any orthogonal set of currents, such as sinusoidal ones, to the actual sample. The voltages are measured for the guessed current set, and compared with those calculated using the forward solver with the same current set and the guessed distribution. The difference voltages can then be used to calculate a better set of currents to distinguish the actual sample distribution from that initially guessed. This new set of currents is then applied to the sample, and also used with the forward solver to obtain two more sets of voltage values, which can then be used to find a third set of even better currents. The process is repeated until the current set is best to distinguish the actual distribution from that guessed, but is not necessarily best to characterize the unknown distribution.

That is done by first solving the inverse problem. That results in an admittivity distribution likely to be much closer to the actual one than the one originally guessed. This new distribution is then used in the forward solver with the best current patterns to this point in order to produce voltages that can again be compared with those measured. A new current set is then calculated from the differences which better distinguishes the actual distribution of admittances from the latest one calculated. Further repetitions of both the procedure for finding the best current set for distinguishing the two distributions of admittivity and the new repetive procedure of calculating distributions that become indistinguishable from those measured with the hardware available result in the best current patterns to characterize the unknown distribution and in the admittivity distribution in the unknown.

An additional feature of this invention is a procedure that permits a reconstruction algorithm that is based on the application of a full set of orthogonal sinusoidal currents, to be used with a full set of orthogonal non-sinusoidal currents by a decomposition process which determines the voltages that would have been measured (with more precise voltmeters than those actually used) had sinusoidal currents been used.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 5 is a flowchart illustrating the procedure for finding the full set of current patterns required to best characterize the distribution of admittivity in an unknown subject.

DESCRIPTION OF THE PREFERRED EMBODIMENTS

Hardware

It is possible to practice this invention using a variety of arrangements of apparatus for the generation of the desired currents for the electrodes and for the measurement of the electrode voltages. One system has been described in U.S. Pat. No. 4,920,490, which is incorporated herein by reference. The system has also been described in the parent patent application Ser. No. 07/734,591. Additionally, an improved apparatus well suited for practicing this invention is described in the parent patent application Ser. No. 08/132,457. A brief description of the apparatus required, is as follows.

Figure 1:
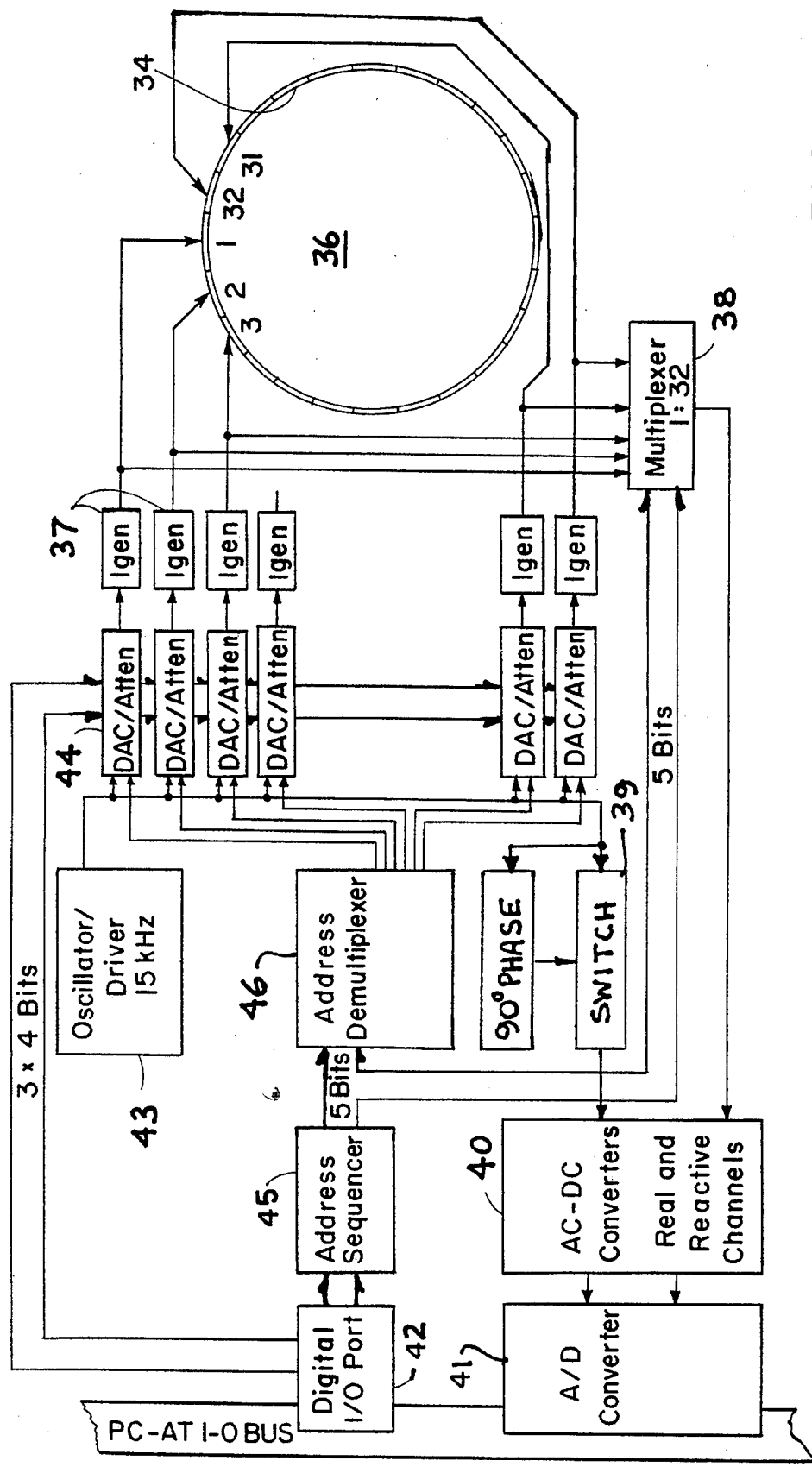
FIG. 1 is a block diagram of the electronic hardware required for an impedance tomography system of the present invention, showing its connection to a set of electrodes around the inside of a circular test tank.

Referring to FIG. 1, there is an array of thirty-two uniformly spaced electrodes 1,2, ... 32 in a plane around the inside of an insulating tank of conductive liquid 36, to simulate a human torso. Objects of contrasting conductivity and permittivity may be introduced into the tank to simulate body organs.

FIG. 1 also shows an array of thirty-two current generators 37 each of which has a separately programmable output level. A single AC voltmeter 40 is attached sequentially through a multiplexer 38 to each electrode of the array in tank 36 for measurement purposes. The voltmeter is of the synchronous, or phase-sensitive type, and may thus measure only components of voltage in phase with the injected currents (real components) or in quadrature with the currents (reactive components) depending on the reference signal supplied through a switch 39.

This special purpose hardware is connected to a microcomputer (e.g. an IBM PC/AT) through a general purpose analog and digital interface board (e.g. a Data Translation DT2800). Synchronization between the instrument and software is accomplished by having the software write clock signals to a digital output port 42. A stable sinusoidal oscillator 43, operating at 15 kHz, is also used.

The 15 kHz oscillator output is buffered and directed to each of the 32 current generators 37. Each generator is based on a three-amplifier configuration, using type LF412 op-amps. The output of each generator is capacitively coupled directly to its output electrode. The wires to the electrodes use actively guarded shields to limit the interelectrode capacitances. Input to each current generator is obtained from a multiplying digital-to-analog converter (DAC) (e.g., an AD7549), operating as a digitally controlled attenuator 44. Digital input for the DACs is obtained through the DT2800 board using a sequence of three four-bit nibbles for each twelve bit word. The DAC is configured as a four quadrant converter so that outputs of all needed magnitudes and both polarities are available.

The digital multiplexer 38 selects one of the thirty-two electrodes and connects it to the input stage of the voltmeter 40. This voltmeter consists of a two-stage high-pass filter followed by a synchronous full-wave demodulator (AD630). The demodulator switches, at either the precise zero crossings of the oscillator and current source signals for obtaining the real component of voltages measured, or at points ninety degrees later, for measuring quadrature components. The selection is schematically shown at the box labeled 90° PHASE, and is made by switch 39, which is under software control. A two-stage low-pass filter follows the demodulator, and the output DC voltage is then sampled by the ADC of an interface board 41, which has 16-bit resolution, programmable gain, and is under software control.

A single digital sequencer 45 addresses both the current generator and the multiplexer for the voltmeter. Under software control, a master reset signal assures that the sequence begins with channel 1. Sequential counters 46 are then used to address the DACs 44 as the digital word representing the desired amplitude for each generator is transmitted. During the read sequence, when the software does not enable the DAC address line, the counter 46 addresses each channel of the multiplexer 38 in sequence and presents the output of each electrode to the voltmeter 40. The A/D converter 41 output is then considered by the software as the desired voltage data, with a 15 ms. interval allowed between conversions for successive electrodes. Each read sequence is normally repeated for the other position of software-operated switch 39, to obtain both real and reactive data.

The current generators 37 are calibrated by loading each channel with known resistors. The gain and offset of each channel can then be stored in software and used to correct the generated currents and the measured values of voltage.

NOSER

Figure 2:
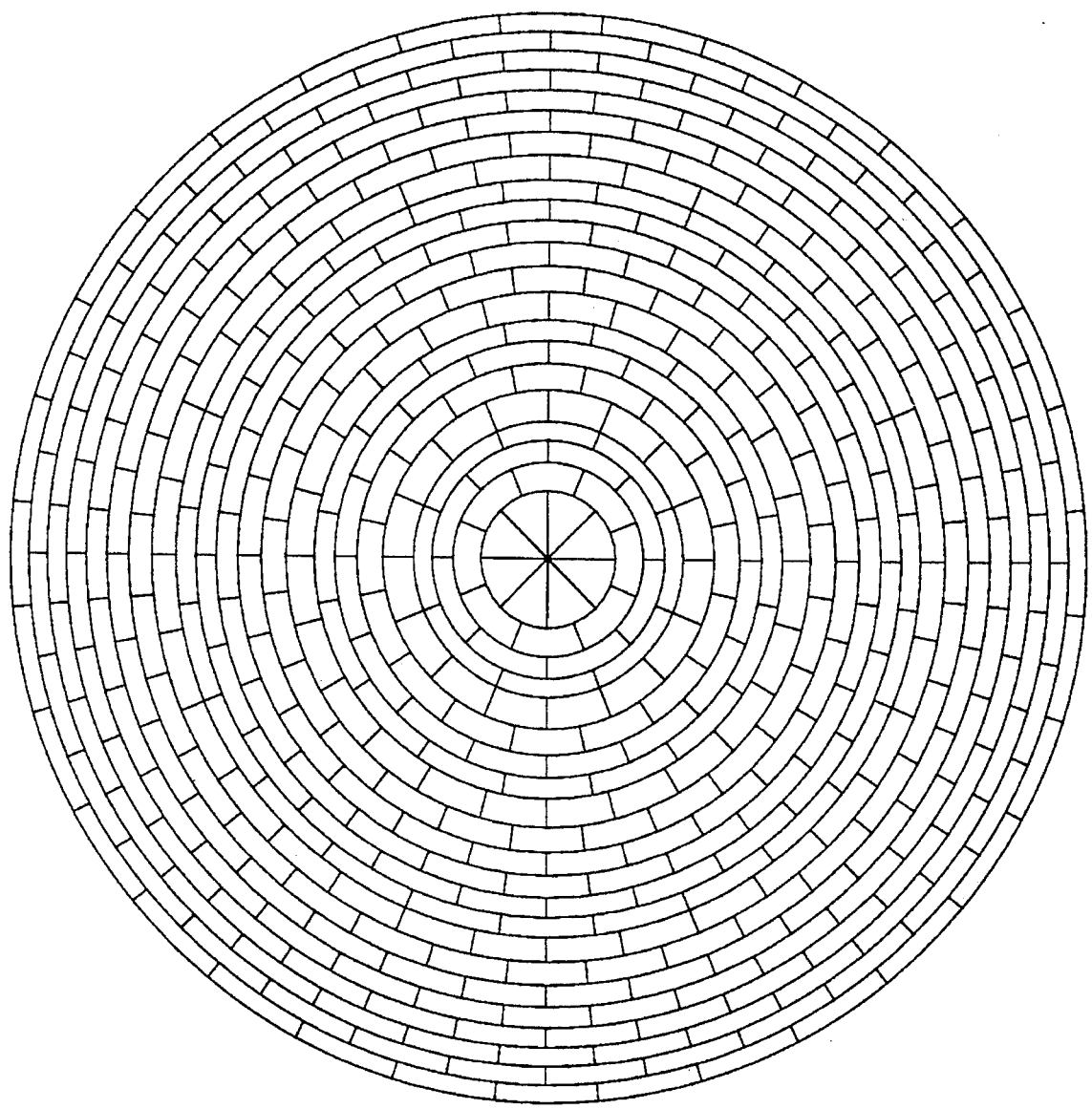
FIG. 2 is a diagram of the "Joshua Tree" grid cell mesh element that are used in the NOSER reconstruction for a thirty two electrode circular system.

The invention uses an algorithm called NOSER (Newton One Step Error Reconstructor) for reconstructing a two-dimensional set of admittivity, conductivity, or permittivity values from measured voltage values and sets of current patterns. This algorithm has been described in detail in "NOSER: An Algorithm for Solving the Inverse Conductivity Problem", by M. Cheney, D. Isaacson, J. Newell, S. Simske, and J. Goble, International Journal of Imaging Systems and Technology, vol. 2, p. 68 (1990). For the present invention, the algorithm has been modified to produce admittivity values, and for complex voltage inputs, so that conductivity and permittivity distributions are direct outputs. For a thirty-two electrode system, each NOSER output is a set of 496 values, each of which is pertinent to one of 496 grid cells of equal area in a circular "Joshua Tree"

mesh, shown in FIG. 2. These mesh values are easily translated into either gray scale or color computer displays. The ovaloid cross section of a human torso is therefore distorted into a circular pattern for display.

Decomposition

Figure 3:
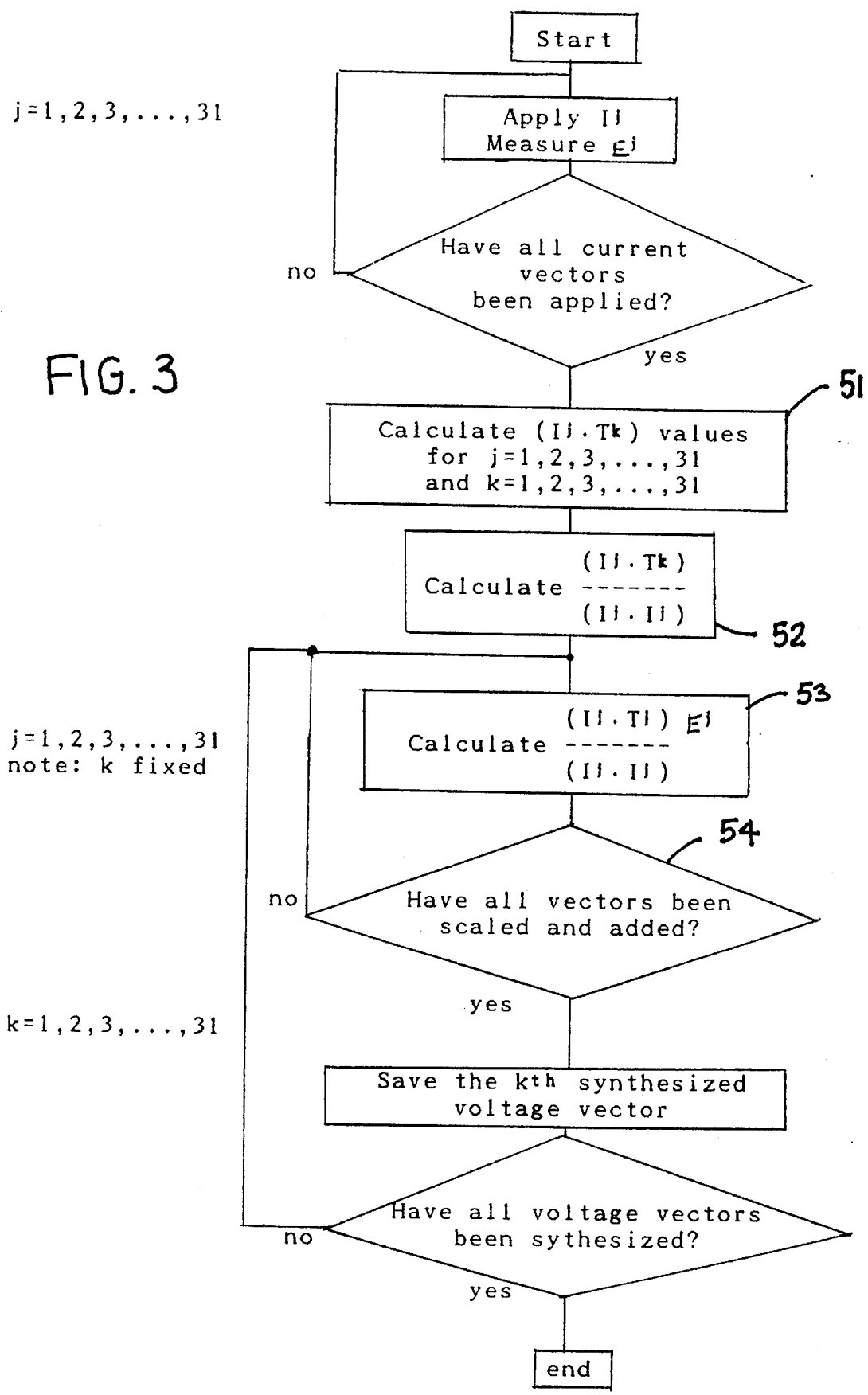
FIG. 3 is a flowchart illustrating the process used to decompose voltage measurements made with non-sinusoidal current patterns and to synthesize equivalent voltages that would have resulted from the application of sinusoidal patterns, that is, a voltage decomposition flowchart.

The NOSER algorithm is based on data from voltages measured when one set of currents that is applied is the lowest frequency spatial cosine, another a spatial sine of lowest frequency, and others are integral multiples of the lowest spatial frequency, the multiple limited by the number of electrodes used. The use of non-sinusoidal current patterns, however, can improve the signal to noise ratio by forcing more currents to flow in regions of the sample that include many variations in admittance. In order to use NOSER with spatial current patterns that are not sinusoidal, such as those that result from algorithms to find optimal sets of current patterns, including those described here, it is useful to decompose the current patterns into their sinusoidal components, and to similarly decompose the measured voltage values in order to use NOSER. A method for doing this for a 32 electrode system is illustrated in the flowchart of FIG. 3.

The non-sinusoidal current patterns are applied in turn, and all thirty-two voltages are measured for each. The voltages may be components in-phase-with or in-quadrature-with the current, or total voltages, whose magnitude can be obtained from the root-mean-square of the components, and angle from the two components. In this discussion we will usually consider only the total voltages for simplicity, so that patterns of admittivity will result. Each set of 32 currents or of voltages can be referred to as a current or voltage vector.

A set of orthonormal current vectors must also be available. These are the coefficients of the set of sinusoidal current patterns normalized to make each vector have unity length. We define the symbols as follows:

j=1, 2, 3, ... 31 k=1, 2, 3, ... 31

Ij is the jth applied current vector

Ej is the jth measured voltage vector

Tk is the kth trigonometric basis vector

Vk is the kth synthesized voltage vector (a.b) denotes the inner product of a and b The equation for the procedure is:

$$Vk = \sum_{j=1}^{31} \frac{(Ij \cdot Tk)}{(Ij \cdot Ij)} Ej$$

At 51 we calculate the inner product of each actual applied current vector with the orthonormal basis vectors. This step calculates scaled Fourier coefficients of the applied current vectors. The coefficients for each j are then divided by the squared norm of the actual current vector, at 52. This is a double normalization procedure, one for the applied currents and one for the measured voltages.

At 53 and 54 we multiply the first measured voltage vector by the first scaled normalized coefficient just calculated to produce the first partial synthesized voltage vector. This process is then repeated by multiplying the second measured voltage vector by the second coefficient to produce the second partial synthesized voltage vector, and repeated a total of thirty-one times. Adding these partial vectors results in the first synthesized voltage vector.

Repeating the procedure again for each additional value of k results in the set of thirty-one synthesized voltage vectors that would have been measured if trigonometric current patterns would have been applied and the voltmeters would have had an improved ratio of signal to noise. This set may then be used to produce a pattern of admittivities using an algorithm such as NOSER. The modified NOSER also finds conductivity and permittivity patterns.

Differences

Figure 4:
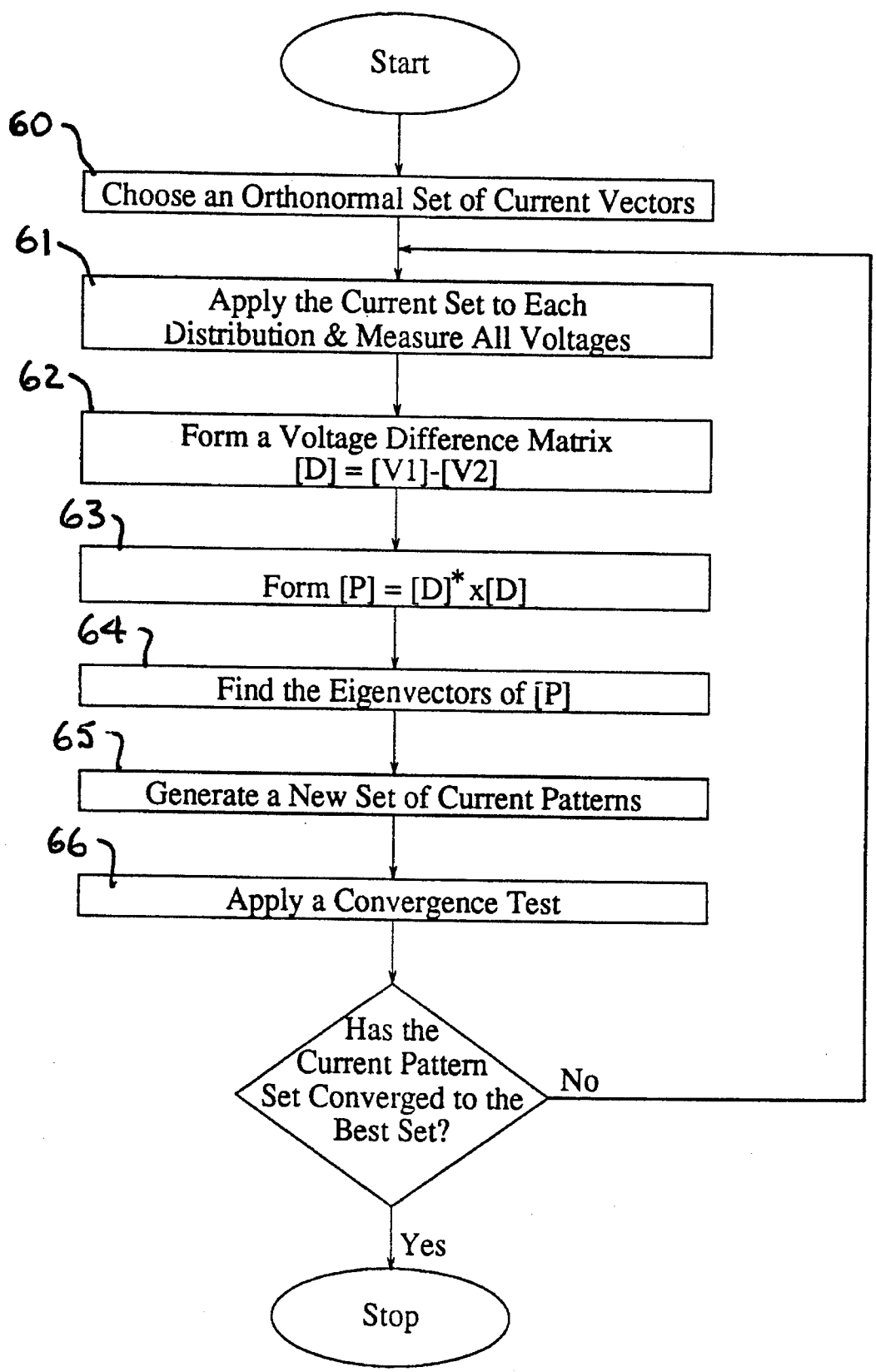
FIG. 4 is a flowchart illustrating the procedure for finding the full set of current patterns that will best distinguish two separate distributions of admittivity from each other.

In order to find the full set of current patterns that will best distinguish two distinct patterns of admittivity, conductivity, or permittivity, the invention proceeds as follows. Refer to the flow chart of FIG. 4. Begin at 60 by guessing any full set of thirty one orthogonal current patterns to begin the process. Usually the canonical sinusoidal patterns are chosen. At 61 apply all of the current patterns in each set to each of the two admittivity patterns in turn, measuring all voltage components, real and reactive, for each pattern. (In many applications, such as in distinguishing conditions in a human body at peak normal inspiration from those at maximum normal expiration, only an appropriate time difference is required.)

At 62 form a voltage difference matrix from the voltages measured under the two conditions, using the magnitude of the phasor difference between corresponding measured voltages. At 63 form the matrix product of the adjoint of the difference matrix with the difference matrix, $[P]=[D]^* \times [D]$. The next step, at 64, is to find the eigenvectors of [P], [E]=[e1 e2 e3 ... ]. At 65 diagonalize [P] by performing a linear transformation [G]=[E]t[P][E], where [G] is a diagonal matrix of the eigenvalues of [P]. In theory, the columns of [E] can be used to find the current vectors, generated at 65, that will best distinguish the two admittivities. In reality, any measurement error, including noise, may make the result less than wholly satisfactory. A simple remedy to improve matters is to repeat the entire procedure beginning with the current patterns just derived, scaled for the same maximum current values as the current set applied previously. Accordingly, at 66 compare the newly derived current set with the one chosen at 60. If the current differences are greater than a preset minimum, as they are likely to be, apply the newly derived set of currents at 61 and repeat the process.

When the current differences between the two patterns are sufficiently small, stop the iteration process. The last set of current patterns is the best, in a practical sense, to distinguish the two admittivity patterns. We then reconstruct the two complex admittivity distributions from the real and reactive voltages measured for both conditions, using the last set of current patterns. The admittivity magnitudes and angles may then be calculated, and the differences between the two reconstructions found, point by point, to permit difference images of admittivity, conductivity, and permittivity (dividing by the angular frequency used) to be displayed on the computer monitor.

Best Overall Picture

The procedure for finding the best set of current patterns to characterize an unknown distribution of admittivity involves some steps that are identical with those just discussed for finding the best patterns to distinguish the difference between two distributions, but also requires procedures for the solution of the problem of calculating the voltages that should theoretically appear at the electrodes for a given set of applied currents and a given distribution of admittivity.

In order to find this set of current patterns we proceed as follows, referring to the flow chart of FIG. 5. Begin by guessing an initial set of orthogonal current patterns, j(0) and guessing an initial admittivity distribution, y(0). (The most common initial guess is that the distributions of conductivity, permittivity, and therefore admittivity are uniform throughout. For circular geometry such as shown in FIG. 1, the current patterns guessed would likely be the canonical set of sines and cosines of increasing spatial frequency.) This step is shown at 70. At this point, 71, k is set to zero signifying the first iteration of the first iterative loop n=o, n being the number of the iterative loop.

Each of the thirty-one current patterns is applied to the electrodes consecutively, and during its application the voltages at all electrodes are measured and recorded, shown at 2 in the flow chart. At 73, the theoretical voltage values that would have resulted from the application of the current patterns j(0) to the admittivity distribution guessed is calculated for the particular geometry involved—in this case circular and two-dimensional. In these two steps the symbol R on the flow chart is an operator that transforms the current vector into a voltage vector.

At 74 we form a voltage difference matrix from the two sets, one measured and one calculated. The differences are first calculated as the phasor differences between the two corresponding voltages for each current pattern. The magnitude of the difference is then taken. At 75 we form the matrix product of the adjoint of the difference matrix with the difference matrix, $[P]=[D]^* \times [D]$. The next step, at 76, is to find the eigenvectors of [P], $[E]=[e1\ e2\ e3\ ...\ ]$. At 77 we diagonalize [P] by performing a linear transformation $[G]=[E]t[P][E]$, where [G] is a diagonal matrix of the eigenvalues of [P].

In theory, the columns of [G] represent the current vectors, generated at 77, that will best distinguish the two admittivities, but in practice it may be necessary to repeat the entire procedure, but beginning with the current patterns just derived, scaled for the same maximum current values as the current pattern set applied previously. Accordingly, at 79 we compare the newly derived current set with the one chosen at 70. If the current differences are greater than a preset minimum, as they are likely to be, we apply the newly derived set of currents at 71 and repeat the process. When the current differences between the two patterns are sufficiently small, we stop the iteration process. Notice that the portion of this procedure from step 74 through step 79 is nearly identical to that described previously to distinguish two distributions of admittivity, the only difference being that here we use the differences between measured and calculated values, rather than between two sets of measured values.

At this point we have generated a set of current patterns that are optimum for distinguishing the actual admittivity distribution from that originally guessed. However, it may not be optimum for characterizing the actual unknown distribution of admittivities. Therefore, at 81 we use a test to determine how close the admittivity pattern calculated is to that originally guessed. This information is available from the latest voltage difference matrix, in step 74.

Assuming that at least one of the voltage differences is higher than is acceptable, we next use an appropriate reconstruction method to produce a new admittances pattern, at 82. The second iteration number, n, is updated at 83 and now a full set of the best current patterns at 79 (after the first set of iterations) is applied to the electrodes and the voltages are measured, at 72. At 73 the theoretical voltages are calculated for that set of current patterns but using the updated distribution of admittivities. The process continues with possible further iterations of the first kind until a new set of "best" current patterns have been produced for the updated admittivity distribution. The test at 81 is made again.

Further updates of admittivities may be needed, each requiring a new "best" set of current patterns until the test result at 81 indicates that, within the limits of our measuring ability, for a defined maximum current value for each pattern, there is an optimal set of currents for an admittivity distribution which is that of the unknown body. The magnitudes of the last admittivity distribution calculated may be displayed on the computer screen either in gray scales or colors as a two-dimensional variation of admittivity values. The conductivity and permittivity distributions may also be calculated and displayed using the appropriate components of the admittivity, as well as the phase angle of the admittivity.

While specific embodiments of the invention have been shown and described in detail to illustrate the application of the principles of the invention, it will be understood that the invention may be embodied otherwise without departing from such principles.

What is claimed is:

1. In an electrical impedance tomography system that includes a body with an array of electrodes on its surface, means for injecting spatial patterns of current into the electrodes consecutively, subject to a limitation on the maximum current in any electrode, and means for measuring the real and reactive voltage components at all the electrodes, an improved method for finding the values of an unknown distribution of permittivities from which images may be formed, comprising:

(a) selecting an arbitrary guessed permittivity distribution and applying an arbitrary guessed set of current patterns to the electrodes to generate a voltage pattern on the array for each current pattern;

(b) measuring all electrode voltages for each current pattern applied which are in quadrature with the current pattern;

(c) calculating values of all theoretical voltages that should have appeared on the electrodes for the body due to the arbitrary set of guessed current patterns and the arbitrary guessed permittivity distribution;

(d) calculating a new set of current patterns based on differences between the measured and calculated voltage values;

(e) calculating the differences between electrode currents of the arbitrary set of current patterns and the calculated new set of current patterns, to form current differences;

(f) if any of the current differences are greater than a selected tolerance, applying the new set of current patterns to the electrode array and repeating steps (b) to (e);

(g) when the current differences are smaller than the selected tolerance, testing whether any of the voltage differences between the measured and calculated values at the electrodes, using the last set of current patterns, are larger than a predetermined value;

(h) if so, computing a new permittivity distribution as a function of the new set of current patterns and the measured voltage values;

(i) repeating steps (b) through (f) using the new permittivity distribution to replace the previously assumed distribution in order to find a set of current patterns that better distinguishes the actual permittivity distribution from the new one; and (j) repeating steps (g) through (i) as many times as are necessary to produce a calculated permittivity distribution whose calculated voltages are substantially identical to those measured.

2. A method according to claim 1, followed by the calculation and display of an image of the permittivity distribution.

* * * * *